Figure 1:
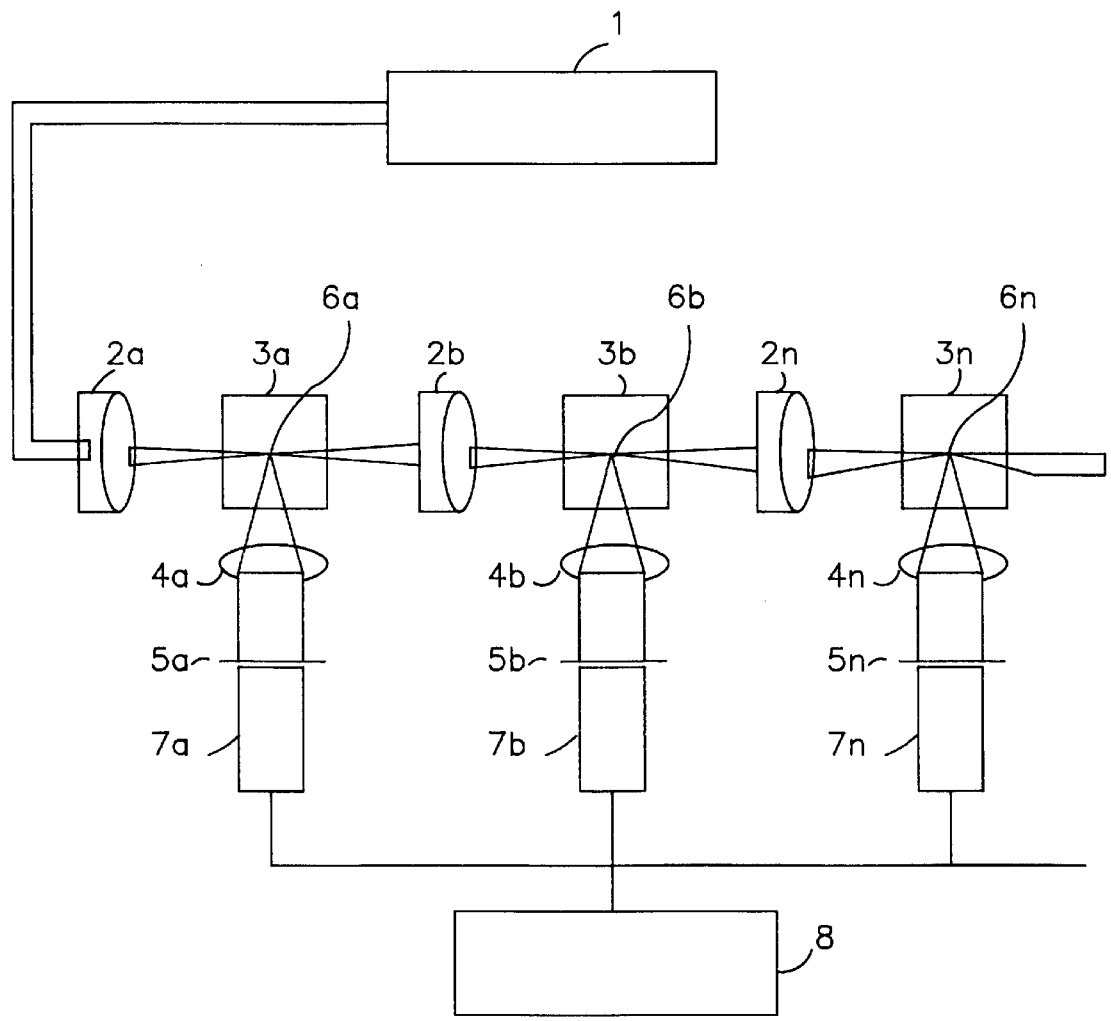

United States Patent [19]
Schrof et al.

[11] Patent Number: 5,815,262
[45] Date of Patent: Sep. 29, 1998

[54] APPARATUS FOR PARALLELIZED TWO-PHOTON FLUORESCENCE CORRELATION SPECTROSCOPY (TPA-FCS), AND THE USE THEREOF FOR SCREENING ACTIVE COMPOUNDS

[75] Inventors: Wolfgang Schrof, Neuleiningen; Jürgen Klingler, Mutterstadt; Dieter Horn, Heidelberg; Elmar Mayer, Augsburg, all of Germany

[73] Assignee: BASF Aktiengesellschaft, Ludwigshafen, Germany

[21] Appl. No.: 700,856

[22] Filed: Aug. 21, 1996

[30] Foreign Application Priority Data

Sep. 7, 1995 [DE] Germany .................. 195 33 092

[51] Int. Cl.$^6$ ........................................ G01J 3/30
[52] U.S. Cl. ................ 356/318; 250/458.1; 250/459.1
[58] Field of Search ........................ 356/318, 317, 356/417; 250/458.1, 459.1, 461.1, 461.2

[56] References Cited

U.S. PATENT DOCUMENTS 5,034,613  7/1991  Denk et al. .................. 250/458.1
5,043,584  8/1991  Koishi .......................... 250/458.1
5,051,162  9/1991  Kambara et al. ............... 250/461.1

OTHER PUBLICATIONS

Madge et al., *Phys. Rev. Lett.*, vol. 29, 1972, pp. 705–708.

Rigler et al., *Phys. Scr.*, vol. 19, 1979, pp. 486–490.

Thompson, *Topics in Fluorescence Spectoscopy*, vol. 1, 1991, pp. 337–410.

Berland et al., *Biophys. J.*, vol. 68, 1995, pp. 694–701.

T. Wilson, *Confocal Microscopy*, Academic Press, London, 1984, pp. 1–64.

*Primary Examiner*—K. Hantis
*Attorney, Agent, or Firm*—Keil & Weinkauf

[57] ABSTRACT

An apparatus for carrying out laser-induced two-photon fluorescence correlation spectroscopy (TPA-FCS), in which a plurality of volumes (6) are delimited or defined in the apparatus in such a way that samples (3) introduced into these volumes can be excited and observed in parallel by means of a single laser (1). Such an apparatus is e.g. used to screen active compounds.

22 Claims, 1 Drawing Sheet

APPARATUS FOR PARALLELIZED TWO-PHOTON FLUORESCENCE CORRELATION SPECTROSCOPY (TPA-FCS), AND THE USE THEREOF FOR SCREENING ACTIVE COMPOUNDS

The present invention relates to an apparatus for carrying out laser-induced two-photon fluorescence correlation spectroscopy (TPA-FCS), and to the use of such an apparatus for screening active compounds.

In the investigation of extremely small and molecular structures, use is made, depending on the area of application and composition or nature of the samples to be analyzed or to be observed, of various spectroscopic methods and corresponding measuring instruments.

FCS is based on the observation of fluorescence from a very small section of a sample volume; this section is known as the observation volume. On average, only a very small number of fluorescent particles are located in this section. The number of particles in the observed volume varies statistically about this mean value owing to thermal diffusion in a still liquid or owing to collective motion in a flowing liquid. The varying number of fluorescent particles in the observation volume results in variations of fluorescence with time.

D. Magde, E. L. Elson, W. W. Webb, Phys. Rev. Lett. 29 (1972), 705–708, R. Riegler, P. Grasselli, M. Ehrenberg, Phys. Scr. 19 (1979), 486–490, and N. L. Thompson, "Topics in Fluorescence Spectroscopy", Vol. 1 (J. R. Lakowicz, Ed.), Plenum Press, New York, 1991, 337–410, describe previous fluorescence correlation spectroscopy measurement arrangements in which a specifically defined observation volume is achieved by means of an arrangement known as confocal microscopy. Confocal microscopy is described in T. Wilson, C. Sheppard, "Theory and Practice of Scanning Optical Microscopy", Academic Press, New York, 1984, and T. Wilson (Ed.), "Confocal Microscopy", Academic Press, London (1984). The arrangement here is a standard microscope in which pinhole diaphragms are arranged in intermediate image planes in the illumination and observation ray paths, so that the image of the illumination diaphragm in the specimen being studied falls precisely on the aperture of the observation diaphragm. This allows the observed volume to be restricted to a very narrow range in the specimen plane, but the instrument complexity is excessively high. In addition, adjustment is complicated and the instrument is susceptible to dirt and vibrations, so that, in particular, measurements cannot be carried out on site.

K. M. Berland, P. T. C. So, E. Graton, "Two-Photon Fluorescence Correlation Spectroscopy: Method and Application to the Intracellular Environment", Biophys. J. 68 (1995), 694–701, describe the use of TPA-FCS in an intracellular environrment. Here, too, a complex microscope is used, but without a pinhole diaphragm in the optical ray path. The disadvantage of this instrument is that the complexity of the microscope again means that on-site measurements are impossible, and in addition only one sample can be studied at a time. The measurement is time-consuming and complicated, since even changing the sample followed by a re-adjustment of the microscope takes a long time. A relatively large-scale study cannot be carried out using a laboratory measurement set-up of this type.

It is an object of the present invention to provide an apparatus for TPA-FCS by means of which samples can be studied more effectively, more quickly and less expensively.

It is a further object of the present invention to provide an apparatus for TPA-FCS and a method which can be employed for screening active compounds.

The object of the invention is consequently achieved by means of an apparatus for carrying out laser-induced two-photon fluorescence correlation spectroscopy (TPA-FCS), where a number of volumes are delimited or defined in the apparatus in such a way that samples introduced into these volumes can be excited by means of a single laser and observed in parallel.

The parallelized design of the measurement apparatus enables a number of samples to be observed simultaneously and alongside one another. The requisite laser radiation is employed in such a way that a number of sample volumes are delimited, and the volumes defined in this way can be studied independently of one another. It is thus also possible, for example, to replace a sample by another without having to interrupt observation of the other samples. In this way, samples can be investigated in industry without the apparatus having to be re-calibrated each time. The entire study is carried out with a single laser, and thus enables more efficient, faster and less expensive study of samples.

In a particularly preferred embodiment of the present invention, an apparatus is proposed in which the laser beam has been modified in such a way that it has a number of focus areas, in particular having a radial dimension of less than 3 $\mu$m, preferably less than 1 $\mu$m, which define the volumes and in which samples can be observed. A laser beam can be modified in various ways: it can be split by a beam splitter and focused in the various ray paths, or it can be focused, for example, in a first focusing area, and straightened again or focused on a second focusing area, etc., by means of a second element. Thus, a "chain" of consecutive focusing areas in whose individual focusing areas or measurement cells the corresponding samples can be observed can easily be produced in a ray path. These two arrangements can also be combined with one another, so that different parallel ray paths can themselves be divided in series one after the other into various focusing areas. The radial dimensions of the generally Gaussian an ray paths of the laser can be selected so that a dimension of less than 2 $\mu$m, preferably less than 1 $\mu$m, is achieved in the shortest dimension in the z-direction. The volume in which the intensity of the laser beam is so high that TPA-FCS can be carried out is thus clearly defined. The quadratic dependence of the fluorescence on the excitation intensity by the laser means that the sample volume to be observed can be restricted to a few $\mu$m$^3$, in particular to less than 1 $\mu$m$^3$. However, this is advantageous in particular in the screening of active compounds, since damage to the constituents in the remainder of the sample is avoided since the laser intensity is much too low to cause damage owing to the extreme focusing of the Gaussian beam. For this reason, the method can also be used in cell organisms. A further advantage is that the small observation volume means that statistical variations about the mean are large enough compared with the mean to enable them to be evaluated.

In a further advantageous illustrative embodiment of the apparatus of the present invention, first objectives or fiber optics, in particular optical objectives, are provided in such a way that the laser beam is focused a number of times. The focusing of the laser beam can in principle be effected in various ways, whether by thermal or optical lenses, by utilizing certain properties of optical waveguides, etc. The use of optical objectives has the advantage that these are easy and inexpensive to procure, and the laser beam is therefore preferably focused by means of optical objectives, ie. for example, lenses or microscope objectives. The smaller the losses suffered by the laser beam on passing through such a lens, the larger the number of series-connected samples that can be observed in parallel. The loss on passing through the sample is negligible. Focusing in the measurement solution can also be achieved by immersion of a monomodal optical fiber.

In a further advantageous embodiment of the novel apparatus, the laser source used is a Ti:sapphire laser, in particular a pulsed mode-coupled laser having preferably pulses with an FWHM (full width @ half minimum) of from 80 to 100 fs. This laser can be operated at a repetition rate of 76 MHz. The choice of the Ti:sapphire laser gives a proven laser which is commercially available and can be used in various wavelength regions. This flexibility within the tuning region is particularly advantageous if different excitation ranges are necessary owing to the nature of the sample or owing to the different labeling of reference substances. The short pulses give peak powers which, even for a low average power level, gives the power in the observation volume which is necessary for TPA-FCS. The repetition rate of 76 MHz enables good registration of the correlation. The laser can be operated, for example, at a mean power of 1 W. A high excitation intensity—a prerequisite for effective two-photon excitation—is achieved by using pulses of high peak power.

In a further advantageous embodiment of the novel apparatus, at least 4 samples, preferably at least 10 samples, in particular up to 100 samples, can be observed in parallel. The number of observable samples depends on the ray geometry achieved, on the losses in the optical elements used, on the power at which the laser is operated, on the transparency of the samples, on the capacity of the evaluation unit, etc. If the corresponding parameters are chosen appropriately, it is even possible to observe up to 1000 samples in parallel.

In a particularly advantageous illustrative embodiment of the present apparatus, at least one photodetector (photomultiplier or semiconductor detector), which can be connected to an evaluation electronics unit, is provided. The fluorescence beam from each sample is imaged on the photodetector, preferably at an angle of 90°. This arrangement allows the fluorescence from the sample to be evaluated by autocorrelation analysis in the subsequent evaluation unit. The mean residence time of the particles in the observation volume can be determined from the standardized autocorrelation function curve measured. A simple distinction between complexed and free particles can be made by determining the 50% value of the standardized autocorrelation function, which shifts to longer times after complexing. In this way, a distinction can easily be made between bound and free reference substance, enabling screening of active compounds.

The volume concentration of fluorescent particles can also be measured by means of the present invention.

The total fluorescence intensity hitting the detector increases in a linear manner with the concentration of the fluorescent particles and quadratically with the peak output of the excitation light source. If the probe is calibrated with a known concentration of particles at constant excitation intensity, unknown concentrations can be determined from its total fluorescence signal.

The fluorescence beam is preferably imaged via a second objective or via a lens, in particular an optical lens, and/or a filter. This enables the intensity and wavelength of the incoming beam to be set and limited correctly. The particle fluorescence is accordingly detected via simple optical imaging by means of lenses or via an optical fiber, in which case the returning fluorescence light is directed via a phase coupler onto the photocatode of a photomultiplier or onto a semiconductor detector. The TPA excitation light is separated from the fluorescence light before the detector using an interference or short-pass filter. The evaluation electronics unit can preferably comprise an amplifier for the signal from the photomultiplier and/or a correlator and/or a computer. The information can thus again be filtered out more clearly, amplified and evaluated. Further components, such as computer cards, digital filters, etc., can be used as desired. Such an embodiment of the present invention is distinguished by the absence of complex microscopic apparatuses.

A further advantageous illustrative embodiment of the present apparatus is distinguished by the fact that a photodetector is provided for each sample, and all the signals from the photodetectors are passed on to a computer. Thus, by using a photodetector, the fluorescence radiation from each sample volume can be registered simultaneously or in parallel per measurement volume, and the resultant signals can be passed on to a computer, where they can be evaluated, for example in the multiplex method. This provides an efficient method of analyzing a number of samples in parallel and of recording and evaluating a large number of signals in parallel.

In a further advantageous embodiment of the apparatus of the present invention, the samples are arranged in a line, and the laser beam passes through the samples in a straight line. The laser beam can be passed through this arrangement with its full energy, so that a sufficiently high intensity of the laser radiation can be achieved with a moderate pump power of the laser, even after subtracting the negligible losses on passing through the optical systems and the individual samples. With this arrangement, the connection of measurement cells in a straight line one after the other results in a simple and relatively reliable set-up.

In a further preferred embodiment of the present invention, an apparatus is provided in which adjusted and focused objectives for the laser beam and/or the fluorescence beam are locked in position. This locking of the optical systems onto the defined sample volumes allows the apparatus to be used industrially: once locked in position, the apparatus no longer requires re-adjustment and realignment after the individual samples are changed. The fluorescence radiation is registered and evaluated by the photomultipliers. The sample can then be replaced, and a further analysis of the new sample can be carried out directly. Since a number of measurement cells are available, n new samples can be introduced into the apparatus simultaneously, enabling industrial evaluation of samples. Automated sample handling thus allows a high sample throughput without the apparatus requiring complicated maintenance and adjustment.

Preferably, the present novel apparatus is used for screening active compounds. This enables the advantages of this novel apparatus to be employed in the analysis of active compounds and thus, for example, a number of active compounds under analysis to be observed and, if the test result is negative, to be excluded directly all at once. The parallel use of a number of measurement cells and automated sample handling allow large numbers of active compounds to be tested within a very short time without the apparatus needing re-adjustment each time. In still liquids, the translational diffusion coefficient of the fluorescent particles and their number concentration can be measured. In particular, changes in the diffusion coefficient, as occur, for example, when another particle attaches to the fluorescent particles, can be measured in this way. It is thus possible to measure complexing reactions of a physical and biochemical nature so long as only one of the participating reaction partners emits inherent fluorescence or has been labeled with a fluorescent dye. If a number of fluorescent particle types are used simultaneously, a distinction can be made between the particle types by selecting the emission spectra of the individual dyes in a suitable manner and selecting the observation wavelength via appropriate detection filters.

The method is also suitable for use with a strong background of other, non-fluorescent particles, since only fluorescent particles are detected. These properties make an instrument of this type suitable for detection of biochemical recognition reactions both directly and also in a displacement experiment.

The simple optical set-up of the method is also suitable for parallel operation of a large number of measurement channels, which considerably shortens the time needed in series studies.

A further use of an apparatus of this invention consists in the study, in particular in a displacement method, of ligand/receptor bonds, preferably for the study of bonds of biological response mediators, in particular growth factor/growth receptor, DNA-binding protein/specific DNA sequence and/or antibody/antigen. This displacement experiment or method can be carried out as follows: in the screening of active compounds by the displacement method, a known fluorescence-labeled reference substance binds to a receptor. If the liquid to be analyzed contains more effective ligands (ie. better active compounds), they displace the initial fluorescence-labeled reference substance. Measurement of the diffusion behavior of the fluorescence-labeled reference substance by TPA-FCS shows an increase in the diffusion motion of the displaced reference substance which is now free (ie. smaller mass and smaller volume). The simple measurement set-up, the short measurement time and the ease of achieving parallelization allow effective screening of active compounds with a high sample throughput.

An illustrative embodiment of the present invention, with further advantageous embodiments, is described below with reference to the drawing.

FIG. 1 shows the diagrammatic set-up of an illustrative embodiment of the present invention with n measurement cells.

The arrangement uses a pulsed laser 1, which is directed via microscope objectives 2a, 2b, 2n through a plurality of measurement cells 3a, 3b, 3n and is focused within these cells. A sample is positioned in each of the focusing areas 6a, 6b, 6n of the measurement cells 3a, 3b and 3n. The particle fluorescence within the samples is detected by optical imaging via lenses 4a, 4b, 4n onto photomultipliers 7a, 7b, 7n. Filters 5a, 5b, 5n are positioned in front of the photomultipliers 7a, 7b, 7n. When a plurality of fluorescent particle types are used and for a suitable choice of the emission spectra of the individual dyes, these detection filters 5a, 5b and 5n can be used to distinguish between the particle types by selecting the observation wavelength. The information from the photomultipliers 7a, 7b and 7n is passed to the evaluation electronics unit 8, where it is processed.

The present invention measures the fluorescent correlation from a very small sample volume by the FCS principle in a simple manner without needing a complex confocal optical system. In particular, the invention is suitable, using simple means, for parallelizing the screening of active compounds by the method of displacement of a fluorescence-labeled reference substance and thus carrying out this screening inexpensively and quickly. Displacement of the bound, fluorescence-labeled reference substance reduces the translation diffusion coefficient significantly. This effect can be utilized for the identification of new active compounds.

The risk of damaging the sample is greatly reduced compared with the one-photon absorption method which was conventional hitherto, since in two-photon absorption the excitation only takes place at the laser focus, the actual measurement volume; otherwise, the laser beam passes through the sample without interaction owing to the long wavelength.

With the aid of two-photon fluorescence correlation spectroscopy, the measurement method for determining the diffusion behavior of fluorescence-labeled particles can be parallelized in a simple manner, and active compound screening can thus be carried out more effectively and less expensively. The light from a single pulsed laser-light source can be passed through a plurality of measurement cells and focused in each of the cells, which, owing to their simple design (standard microscope objective or monomodal optical fiber for excitation and extremely simple optics for detection), can be constructed very inexpensively. Compared with conventional fluorescence correlation spectrometers, which are based on the use of a confocal microscope with the above-described disadvantages, the optical design and adjustment are simplified and the costs and time required for parallelization are drastically reduced.

The use of the method and set-up enables inexpensive and time-effective screening of active compounds in general and especially in the parallelized version.

Complex, sensitive and expensive confocal optics are totally unnecessary. The measurement can also be carried out in sample containers which are unsuitable for microscopy. Parallelized measurement is possible in a simple and inexpensive manner.

The risk of damage to the sample is greatly reduced compared with the one-photon absorption method which was conventional hitherto, since in two-photon absorption the electronic excitation only takes place at the laser focus, the actual measurement volume; otherwise, the laser beam passes through the sample without interaction owing to the long wavelength, which is outside the linear absorption spectrum.

We claim:

1. An apparatus for simultaneously screening a plurality of samples of active compounds by carrying out laser-induced two-photon fluorescence correlation spectroscopy (TPA-FCS), comprising a plurality of volumes (6a, 6b . . . 6n) which are delimited or defined by consecutively focusing a single laser beam into the volumes, thereby creating a chain of volumes in series, and thereby allowing introduction, excitement, and observation of one sample of the plurality of samples in each of the volumes.

2. The apparatus of claim 1, wherein the volumes have a radial dimension of less than 3 $\mu$m.

3. The apparatus of claim 1, further comprising a plurality of first objectives or fiber optics (2a, 2b . . . 2n) in the laser beam provided in such a way that the laser beam is focused on each of the volumes.

4. The apparatus of claim 1, wherein the laser beam is created by a Ti:sapphire laser.

5. The apparatus of claim 1, comprising from 4 to 100 volumes.

6. The apparatus of claim 1, further comprising at least one photodetector (photomultiplier or semiconductor detector) (7a, 7b . . . 7n) which can be connected to an electronics unit (8) and on which a fluorescence beam from each sample (3a, 3b . . . 3n) is imaged.

7. The apparatus of claim 6, wherein each fluorescence beam is imaged on each photodetector via at least one second objective.

8. An apparatus as claimed in claim 1, wherein a photodetector (7a, 7b . . . 7n) is provided for each sample (3a, 3b . . . 3n) and all the signals from the photodetectors are passed on to a computer.

9. An apparatus as claimed in claim 1, wherein the samples (3a, 3b . . . 3n) are arranged in a line, and a laser beam passes through the samples in a straight line.

10. The apparatus of claim 7, wherein the second objectives are locked in position in the apparatus.

11. The apparatus of claim 6, which includes an evaluation electronics unit (8), which comprises an amplifier for the signal from the at least one photodetector and/or a correlator and/or a computer.

12. The apparatus of claim 6, wherein the fluorescence beam from each sample (3a, 3b . . . 3n) is imaged at right angles to the laser beam.

13. The apparatus of claim 1, comprising a first optical objective for each volume arranged to focus said laser beam into each of the volumes.

14. The apparatus of claim 13, wherein each first optical objective is locked in position in the apparatus.

15. The apparatus of claim 4, wherein the laser is a pulsed, mode-coupled laser, having pulses with an FWHM (full width @ half minimum) of from 80 to 100 fs.

16. A method of screening samples of active compounds contained in a plurality of sample volumes, said method comprising:

(a) passing a laser beam through each of said plurality of sample volumes, (b) focusing said laser beam into each of said plurality of sample volumes, (c) observing by laser-induced two-photon fluorescence correction spectroscopy (TPA-FCS) each of said plurality of sample volumes.

17. A method of claim 16, wherein changes in the diffusion coefficient of fluorescent particles in said sample volumes are measured.

18. A method in accordance with claim 16, wherein said sample volumes contain ligand/receptor bonds.

19. A method in accordance with claim 16, wherein said sample volumes contain bonds of biological response mediators.

20. A method in accordance with claim 19, wherein said bonds are bonds of growth factor/growth receptor, DNA-binding protein/specific DNA sequence and/or antibody/antigen.

21. A method in accordance with claim 16, wherein said method is a displacement method.

22. A method in accordance with claim 16, wherein said laser beam is focused through optical objectives.

* * * * *